United States Patent
Hajaj et al.

(10) Patent No.: US 6,941,164 B2
(45) Date of Patent: *Sep. 6, 2005

(54) MULTIMODALITY IMAGING SYSTEM

(75) Inventors: Benny Hajaj, Zoran (IL); Hernan Altman, Nesher (IL); Sergio Steinfeld, Haifa (IL); Yaron Hefetz, Herzeliya (IL)

(73) Assignee: Elgems Ltd., Tirat Hacarmel (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/841,439

(22) Filed: May 10, 2004

(65) Prior Publication Data

US 2004/0210126 A1 Oct. 21, 2004

Related U.S. Application Data

(63) Continuation of application No. 09/718,507, filed on Nov. 24, 2000, now Pat. No. 6,754,519.

(51) Int. Cl.$^7$ .................................................. A61B 5/05
(52) U.S. Cl. ...................................................... 600/407
(58) Field of Search ................................ 600/407–472; 378/197, 4, 21–27, 49, 87, 92, 205; 128/897

(56) References Cited

U.S. PATENT DOCUMENTS

| 4,710,876 A | * | 12/1987 | Cline et al. .................. 345/423 |
| 6,205,347 B1 | * | 3/2001 | Morgan et al. ............. 600/407 |
| 6,754,519 B1 | * | 6/2004 | Hefetz et al. ................ 600/407 |

* cited by examiner

*Primary Examiner*—Ali Imam
(74) *Attorney, Agent, or Firm*—AlphaPatent Associates Ltd.; Daniel J. Swirsky

(57) ABSTRACT

A multimodality imaging system including a plurality of imaging systems, and at least one rail upon which at least one of the imaging systems is slidingly mounted.

9 Claims, 2 Drawing Sheets

MULTIMODALITY IMAGING SYSTEM

CROSS-REFERENCE TO RELATED APPLICATIONS

This application is a continuation of U.S. patent application Ser. No. 09/718,507, now U.S. Pat. No. 6,754,519, filed on Nov. 24, 2000, entitled "Multimodality Imaging System," and incorporated herein by reference in its entirety.

FIELD OF THE INVENTION

The present invention relates generally to patient positioning systems for multimodality imaging systems, and particularly to maintaining linear and angular registration between a plurality of imaging systems of a multimodality imaging system.

BACKGROUND OF THE INVENTION

Imaging systems acquire images of a patient, such as images of a suspected tumor, for diagnosis and subsequent treatment or therapy. Commonly used medical imaging systems include fluoroscopy, computerized tomography (CT), magnetic resonance (MRI) or positron emission tomography (PET), for example.

Many imaging systems employ a patient table or couch (the terms being used interchangeably herein throughout the disclosure and claims) upon which a patient is supported throughout the imaging process. In general, the patient lies on the table, which may move along a first axis (generally the azimuth axis). The theoretical isocenter is defined as the symmetry axis of the gantry. The imaging system identifies the spatial coordinates of the suspected tumor, with reference to the isocenter, or for guiding the planning of surgery or other treatments. Accurate measurement of these coordinates is crucial for subsequent treatment of the suspected tumor, because the position of the tumor, as defined by the imaging system, is then used as the target for irradiation, such as by a stereotactic radiotherapy system. A typical stereotactic radiotherapy system uses a linear accelerator (LINAC) gantry, which rotates about the longitudinal axis of the table. It is essential that the isocenter of the LINAC gantry be as close possible to the isocenter of the imaging system.

Multimodality imaging systems employ a plurality of imaging systems, such as CT and PET imaging heads or gantries aligned along a common longitudinal axis. The patient registration should be the same for both imaging systems. Specifically, the isocenter of the first imaging system should be aligned as accurately as possible with the isocenter of the second imaging system. This is not a trivial task because no mechanical assembly is perfect, due, inter alia, to tolerances and the fact that mechanical parts are not infinitely stiff.

Some systems have attempted to solve this problem by means of a fixed alignment between the two imaging systems during the manufacturing process of the multimodality system. Basically this approach places high restrictions on tolerances and mechanical accuracies during production and assembly of the system. This method has the drawback of being quite expensive. Another approach is the use of a fixed calibration during assembly of the system. An accurate jigging fixture is used to align the two imaging systems with each other. This approach is less expensive than the first approach, but still has a disadvantage of being time-consuming. Both methods have a further disadvantage, in that if it is required to service one or more of the imaging systems, the systems must be re-aligned, which can be a cumbersome, time-consuming and tedious task.

SUMMARY OF THE INVENTION

The present invention seeks to provide improved apparatus that substantially maintains linear and angular registration between a plurality of imaging systems of a multimodality imaging system.

In the present invention, at least one of the imaging systems is slidingly mounted on a set of one or more rails. The rails may be adjusted linearly along a vertical axis perpendicular to the longitudinal axis of the rails, and adjusted rotationally about a third axis perpendicular to the two aforementioned axes. This provides several advantages. First, mounting one or more of the imaging systems on rails enables separating the imaging systems easily and quickly for servicing. Secondly, after servicing there is generally no need for time-consuming recalibration after re-positioning the displaced imaging system to its original position. Third, since the rails are capable of linear and rotational adjustment, the invention enables quick and straightforward initial calibration and alignment of the imaging systems with each other.

There is thus provided in accordance with a preferred embodiment of the present invention a multimodality imaging system including a plurality of imaging systems, and at least one rail upon which at least one of the imaging systems is slidingly mounted.

In accordance with a preferred embodiment of the present invention the at least one rail is adjustable linearly along a vertical axis generally perpendicular to a longitudinal axis of the at least one rail.

Further in accordance with a preferred embodiment of the present invention the at least one rail is adjustable rotationally about another axis generally perpendicular to the vertical axis and the longitudinal axis.

Additionally in accordance with a preferred embodiment of the present invention a leveling device is provided which is operative to adjust a height of at least one of the imaging systems generally along a vertical axis generally perpendicular to a longitudinal axis of the at least one rail.

In accordance with a preferred embodiment of the present invention an isocenter of one of the imaging systems is substantially collinear with an isocenter of another of the imaging systems.

Further in accordance with a preferred embodiment of the present invention one of the imaging systems includes a computerized tomography (CT) imaging system, and another of the imaging systems includes a positron emission tomography (PET) imaging system.

There is also provided in accordance with a preferred embodiment of the present invention a multimodality imaging system including a plurality of imaging systems, and a set of wheels attached to at least one of the imaging systems by means of an adjustable suspension assembly mounted to the at least one of the imaging systems.

In accordance with a preferred embodiment of the present invention the suspension assembly includes a linkage member pivotally mounted to the at least one of the imaging systems.

Further in accordance with a preferred embodiment of the present invention a leveling device is connected to the linkage member.

Still further in accordance with a preferred embodiment of the present invention an arresting device is adapted to fix at least one of the imaging systems at a predetermined location.

There is also provided in accordance with a preferred embodiment of the present invention a method for installing a multimodality imaging system, including providing at least one rail upon which at least one imaging system is slidingly mountable, aligning a first imaging system, such that the first imaging system is substantially aligned and leveled with a longitudinal axis of the at least one rail, and slidingly mounting a second imaging system on the at least one rail.

In accordance with a preferred embodiment of the present invention the first imaging system is also mounted on the at least one rail.

Further in accordance with a preferred embodiment of the present invention the second imaging system is aligned with the first imaging system such that an isocenter of the first imaging system is substantially collinear with an isocenter of the second imaging system.

Still further in accordance with a preferred embodiment of the present invention the imaging systems are separated from each other by sliding the second imaging system along the at least one rail.

Additionally in accordance with a preferred embodiment of the present invention at least one of the imaging systems is serviced after separating them from each other. The imaging systems may be slid back towards each other after servicing.

BRIEF DESCRIPTION OF THE DRAWINGS

The present invention will be understood and appreciated more fully from the following detailed description taken in conjunction with the drawings in which.

DETAILED DESCRIPTION OF A PREFERRED EMBODIMENT

Figure 1:
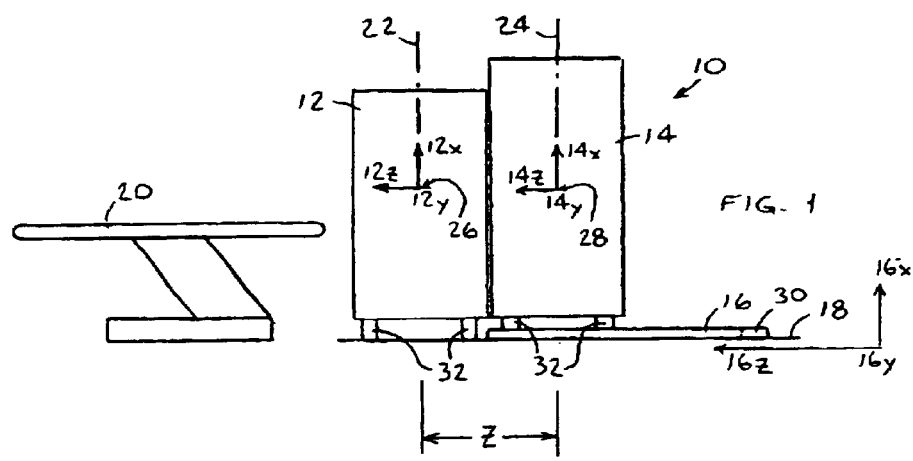
FIGS. 1 and 2 are simplified side-view illustrations of a multimodality imaging system, constructed and operative in accordance with a preferred embodiment of the present invention, with two imaging systems respectively adjacent to one another and separated from each other.
Figure 2:
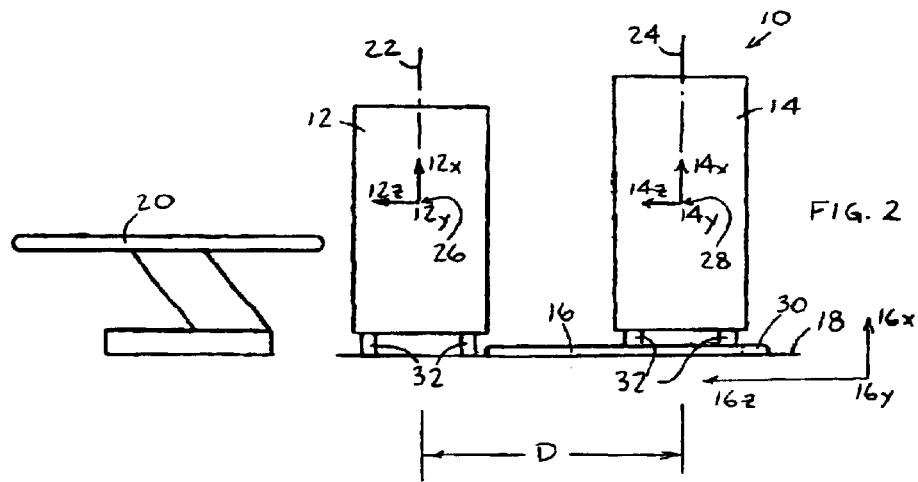

Reference is now made to FIGS. 1 and 2, which illustrate a multimodality imaging system 10, constructed and operative in accordance with a preferred embodiment of the present invention.

Multimodality imaging system 10 includes a plurality of imaging systems. In the illustrated embodiment, there is a first imaging system 12, such as a computerized tomography (CT) imaging system, and a second imaging system 14, such as a positron emission tomography (PET) imaging system. One or both of the imaging systems is preferably slidingly mounted on a set of one or more rails 16, fixedly attached to a floor 18. In the illustrated embodiment, there is a pair of generally parallel rails 16, although any other number of rails may be employed to carry out the invention.

Throughout the specification and claims, "slidingly mounted on one or more rails" is understood to comprise the situation wherein the imaging systems are provided with grooves in which sit the one or more rails, as well as the situation wherein the imaging systems are provided with one or more elongate rail-like protrusions which slide in female tracks, or any combination or equivalent thereof. Wheels or ball bearings may be used to reduce friction.

First imaging system 12 has a coordinate system of three mutually orthogonal axes, 12x, 12y and 12z, and second imaging system 14 has a coordinate system of three mutually orthogonal axes, 14x, 14y and 14z (12y and 14y extending perpendicularly out of the plane of FIG. 1). A patient table 20 is preferably provided for selectively bringing a patient (not shown) into a viewing plane 22 of first imaging system 12 (in the plane of 12x and 12y), or a viewing plane 24 of second imaging system 14 (in the plane of 14x and 14y). As discussed hereinabove, in order to provide images of a portion of the patient, that portion should be at the isocenter of the imaging system. In the illustrated embodiment, the isocenter 26 of first imaging system 12 is at the origin of the coordinate system of axes 12x, 12y and 12z. Similarly, the isocenter 28 of second imaging system 14 is at the origin of the coordinate system of axes 14x, 14y and 14z. The present invention facilitates collinear alignment of isocenters 26 and 28 of imaging systems 12 and 14, as described further hereinbelow.

Rails 16 may be adjusted linearly along a vertical axis 16x, generally perpendicular to a longitudinal axis 16z of the rails 16. The adjustment may be made by means of a leveling device 30, e.g., jackscrews or any other equivalent device. Additionally, rails 16 may be adjusted rotationally about a transverse axis 16y, generally perpendicular to axes 16x and 16z. The rotational adjustment may be made, for example, by selectively raising or lowering some of the jackscrews to provide the necessary tilt.

One or both of imaging systems 12 and 14 are also preferably provided with a leveling device 32, e.g., jackscrews or any other equivalent device. Leveling device 32 adjusts the height or level of the imaging system generally along axis 12x or 14x, and may be used to make rotational adjustments about axis 12y or 14y, in a manner similar to that described for leveling device 30.

A preferred procedure for installing multimodality imaging system 10 is now described. The first imaging system 12 is installed, either on the floor 18 or on rails 16, and may be initially leveled by means of leveling device 32. The second imaging system 14 is then installed on rails 16, such that second imaging system 14 can slide away from first imaging system 12 (the position shown in FIG. 2) or can slide towards and be adjacent first imaging system 12 (the position shown in FIG. 1). Imaging systems 12 and 14 are then aligned for parallelism and level by suitable adjustment of leveling devices 32 and/or suitable adjustment of rails 16 by means of leveling device 30. A desired longitudinal spacing between the two systems, indicated by reference letter Z in FIG. 1 and reference letter D in FIG. 2, may be adjusted by sliding either one of the imaging systems on rails 16.

First and second imaging systems 12 and 14 then scan registration phantom images, which are superimposed and compared to check the collinear alignment of the isocenters of the two imaging systems. A final adjustment and calibration is then performed to fine-tune the alignment between the two imaging systems 12 and 14.

Servicing the two imaging systems 12 and 14 is straightforward. The imaging systems 12 and 14 are simply separated from each other by sliding second imaging system 14 along rails 16. Alternatively or additionally, first imaging system 12 may be slid along rails 16, if it is mounted on rails 16. Once separated, any of the imaging systems may then be serviced. After servicing, the imaging systems are simply slid back to their original positions. There is generally no need for recalibration after re-positioning the imaging systems to their original positions, because rails 16 help maintain the original calibration.

Figure 3:
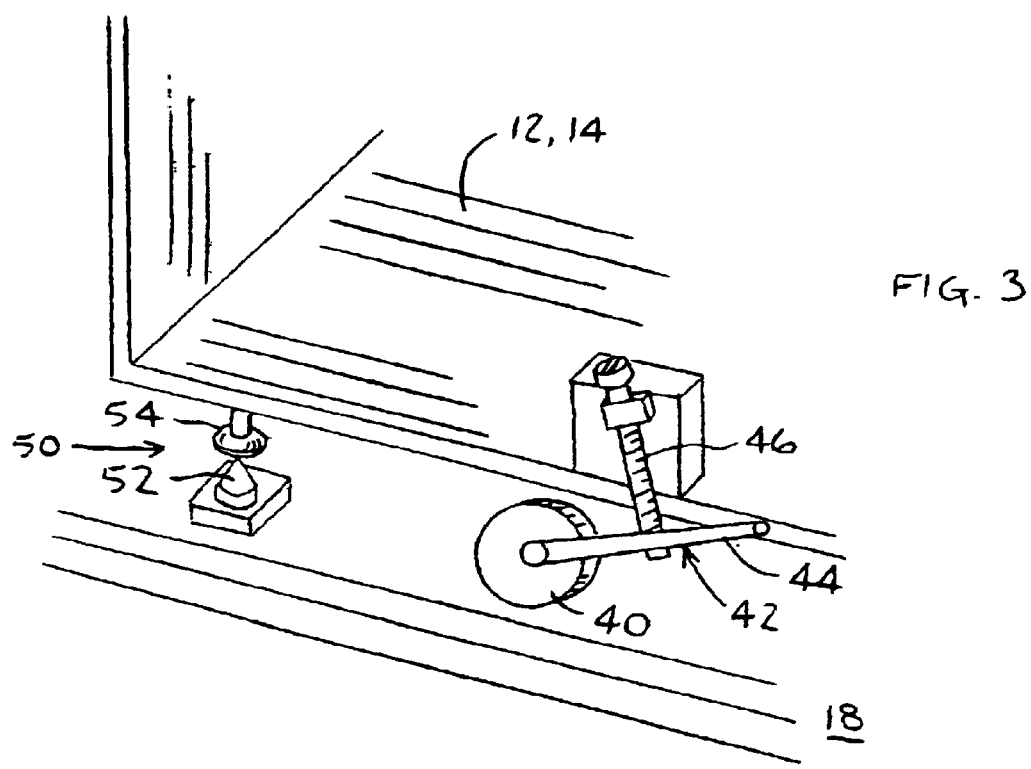
FIG. 3 is a simplified pictorial illustration of a portion of a multimodality imaging system, constructed and operative in accordance with another preferred embodiment of the present invention

Reference is now made to FIG. 3 which illustrates an alternative embodiment for maintaining linear and angular registration between a plurality of imaging systems, constructed and operative in accordance with another preferred embodiment of the present invention. In this embodiment, one or both of the imaging systems is mounted on a set of wheels 40, by means of an adjustable suspension assembly 42. Suspension assembly 42 preferably includes a linkage member 44 pivotally mounted to a lower portion of one of the imaging systems 12 or 14. The angle of the linkage member 44 with respect to the horizontal may be adjusted by a leveling device 46, such as an adjustment screw or equivalent device. There is preferably a set of four such wheels 40, two one each side of the imaging system 12 or 14.

By mounting one or both of the imaging systems on wheels 40, the two imaging systems may be rolled away from each other (corresponding to the position shown in FIG. 2), or conversely, rolled towards each other (corresponding to the position shown in FIG. 1). As described hereinabove, imaging systems 12 and 14 are aligned for parallelism and level by suitable adjustment of leveling devices 32 and/or suitable adjustment of wheels 40 by means of suspension assembly 42 and leveling device 46.

The wheeled imaging system may be locked into position by an arresting device 50. One example of arresting device 50 is shown in FIG. 3. In the illustrated embodiment, arresting device 50 includes a generally conical boss 52 fixedly mounted on floor 18. A coupling device 54 is preferably fixedly mounted to and protrudes from underneath the imaging system 12 or 14. Bosses 52 are preferably attached to floor 18 to correspond to the predetermined stopping places for the imaging systems. When the imaging system is rolled to the desired stopping place, coupling device 54 mates with boss 52. Bosses 52 are also preferably accurately aligned with each other to correspond with the proper alignment of the two imaging systems with each other. Thus, arresting device 50 not only maintains the correct spacing between the imaging systems, it also helps in registration of the two imaging systems with each other.

It will be appreciated by person skilled in the art, that the present invention is not limited by what has been particularly shown and described herein above. Rather the scope of the present invention is defined only by the claims which follow:

What is claimed is:

1. A method for installing a multimodality imaging system, comprising:

providing at least one rail;

aligning said first imaging system, such that said first imaging system is substantially aligned and leveled with a longitudinal axis of said at least one rail;

slidingly mounting a second imaging system on said at least one rail; and aligning said second imaging system with said first imaging system such that an isocenter of said first imaging system is substantially collinear with an isocenter of said second imaging system.

2. The method according to claim 1 wherein said first imaging system is also mounted on said at least one rail.

3. The method according to claim 1 and further comprising:

separating said imaging systems from each other by sliding said second imaging system along said at least one rail; and servicing at least one of said imaging systems after separating them from each other.

4. The method according to claim 3 and further comprising sliding back said second imaging system towards said first imaging system after servicing at least one of said imaging systems.

5. A multimodality imaging system comprising:

a plurality of imaging systems, wherein the isocenters of each of said imaging systems are substantially collinear; and at least one rail upon which at least one of said imaging systems are slidingly mounted, wherein said at least one rail is adjustable rotationally about an axis generally perpendicular to a longitudinal axis of said at least one rail and a vertical axis generally perpendicular to said longitudinal axis.

6. The multimodality imaging system according to claim 5 and further comprising a leveling device operative to adjust a height of at least one of said imaging systems generally along said vertical axis generally perpendicular to said longitudinal axis of said at least one rail.

7. The multimodality imaging system according to claim 5 wherein one of said imaging systems comprises a computerized tomography (CT) imaging system, and another of said imaging systems comprises a positron emission tomography (PET) imaging system.

8. A multimodality imaging system comprising:

a plurality of imaging systems, wherein the isocenters of each of said imaging systems are substantially collinear; and a set of wheels attached to each at least one of said imaging systems by means of an adjustable suspension assembly mounted to said imaging system, wherein said suspension assembly comprises a linkage member pivotally mounted to said imaging system.

9. The multimodality imaging system according to claim 8 and further comprising a leveling device connected to said linkage member.

* * * * *